US005798381A

United States Patent [19]

Biard et al.

[11] Patent Number: 5,798,381
[45] Date of Patent: Aug. 25, 1998

[54] BIOLOGICALLY ACTIVE BISTRAMIDES, PROCESS FOR THEIR PRODUCTION AND THEIR APPLICATIONS IN THERAPY

[75] Inventors: Jean-Francois Biard, Nantes; Dominique Cortadellas, Montpellier Cedex 1; Cécile Debitus, Noumea, all of France; Dominique Laurent, La Paz, Bolivia; Cristos Roussakis, Nantes; Jean-Francois Verbist, Aigrefeuille Sur Maine, both of France

[73] Assignee: Institut Francais de Recherche Scientifique pour le Development en Cooperation (Orstom), Paris, France

[21] Appl. No.: 513,923

[22] PCT Filed: Mar. 8, 1994

[86] PCT No.: PCT/FR94/00256

§ 371 Date: Mar. 4, 1996

§ 102(e) Date: Mar. 4, 1996

[87] PCT Pub. No.: WO94/20503

PCT Pub. Date: Sep. 15, 1994

[30] Foreign Application Priority Data

Mar. 8, 1993 [FR] France ................................ 93 02662
Jun. 29, 1993 [FR] France ................................ 93 07925

[51] Int. Cl.[6] .......................... C07D 403/04; A61K 31/55
[52] U.S. Cl. ........................ 514/456; 514/453; 514/451; 549/334
[58] Field of Search ........................... 549/334; 514/456, 514/451, 453

[56] References Cited

FOREIGN PATENT DOCUMENTS 2 063 068   6/1981   United Kingdom .
90/05731   5/1990   WIPO .

OTHER PUBLICATIONS

Dunkel, R. et al. Analytical Chemistry, 64, 24, Dec., 1992, pp. 3150–3160.
Foster et al. Journal of the American Chemical Society 114(3):1110–1111 (1992).
Chemical Abstracts 115(23):34 (1991), abstract No. 247630a.

*Primary Examiner*—Robert T. Bond
*Attorney, Agent, or Firm*—Nixon & Vanderhye, P.C.

[57] ABSTRACT

Bistramide derivatives with virtually no toxic effects, of formula (I) wherein —$R_1$, X, Y and $R_2$ are a saturated or unsaturated hydrocarbonaceous chain having from 1 to 20 carbon atoms, substituted by at least one —OH group and/or a ketone function, including, if need be, at least one ring (a), the ring including one more unsaturations; —$R_3$, $R_4$ and $R_5$ are the same or different and are selected from hydrogen, alkyl or alkoxy radicals having from 1 to 4 carbon atoms, a group —COOH, —OH, —NH or —$NO_2$, or a halogen atom. The invention also concern bistramide derivatives of formula (I) such as ethers or esters and their isomers, excluding A, B and C bistramides. Said bistramides are useful especially as drugs having a cytostatic effect, in particular as antitumour or anti-parasitic drugs.

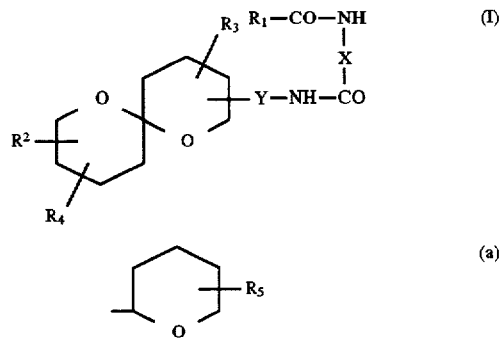

33 Claims, 1 Drawing Sheet

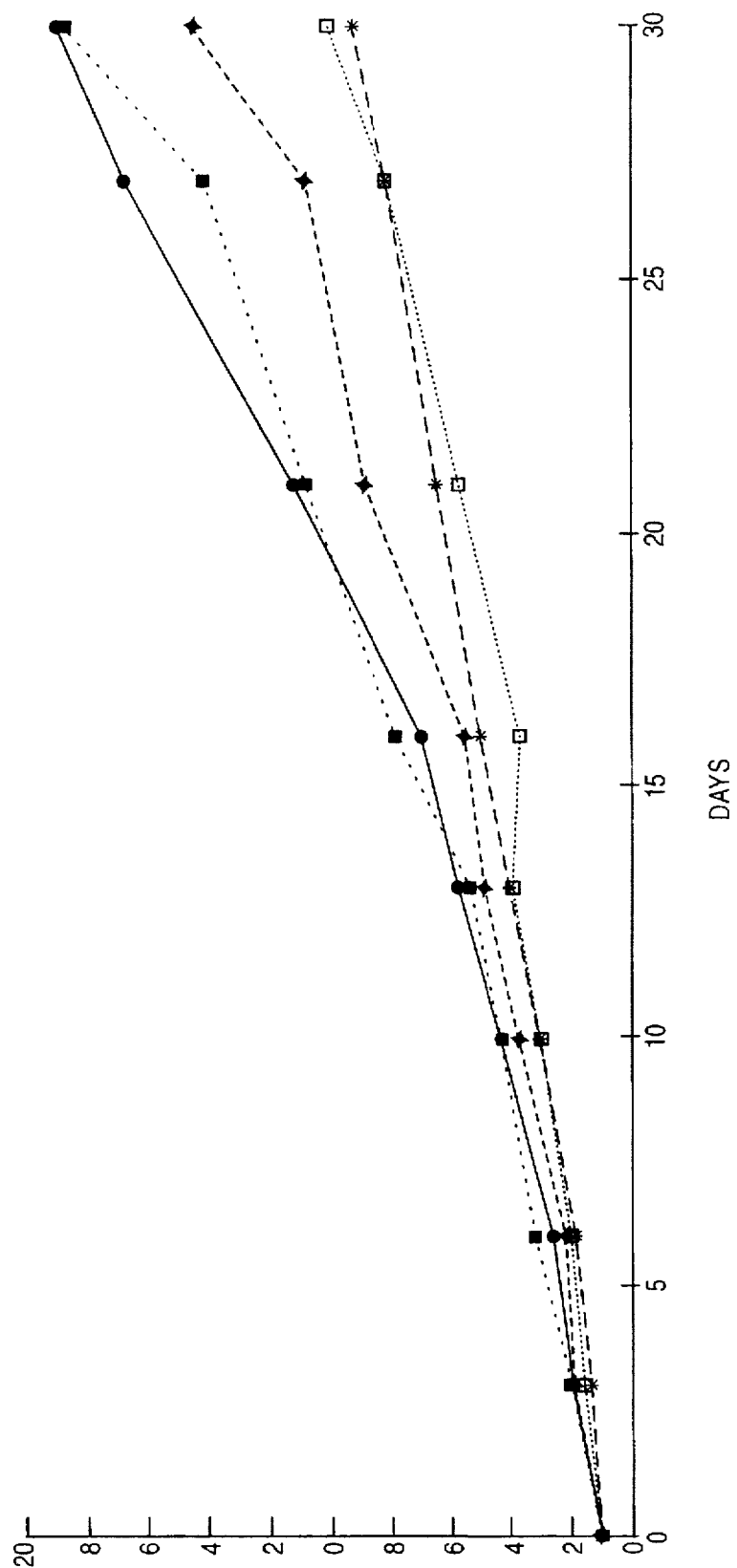

5,798,381

BIOLOGICALLY ACTIVE BISTRAMIDES, PROCESS FOR THEIR PRODUCTION AND THEIR APPLICATIONS IN THERAPY

A subject of the invention is new derivatives of bistramides, process for their production and their applications in therapy.

Bistramides are so called by analogy with a marine organism from which they can be extracted, namely the ascidia *Lissoclinum bistratum* which lives in symbiosis with its prochlorons.

Several bistramides have already been described, in particular bistramides A, B and C.

Their chemical structure, which is complex, has only recently been elucidated (see article by Foster et al. in J.A.C.S. 1992, 114). It corresponds to formula (A) as follows:

Formula A for bistramide A for bistramide B for bistramide C

Interest in these products results, in a general manner, from the strong cytostatic activity they present in particular in vitro. However, their high cytotoxicity and high toxicity in vivo does not allow exploitation of their properties to be envisaged for uses such as medicaments.

The $LD_{50}$ of these bistramides is in fact of the order of 1.7 mg/kg (measured in mice, after injection of the product by intravenous route as a single dose).

Work by the inventors on marine invertebrates, in particular on the ascidia *Lissoclinum bistratum* Sluiter, accompanied or not by its prochloron symbiotes, have lead them to perfecting the specific extraction conditions allowing new bistramides to be isolated having diverse biological activities which are of great interest.

In a surprising manner, study of these new bistramides showed that they were endowed with a cytostatic effect in vitro and therapeutic effects in vivo, but that, contrary to the bistramides mentioned above, their cytotoxicity and their toxicity in vivo were much weaker, even non-existent, which permits their use in therapy.

Therefore, an aim of the invention is to provide new derivatives having a bistramide-type structural skeleton.

It is also an aim of the invention to provide a process for the production of these products by extraction from *L. bistratum* and/or their prochlorons.

Also the invention relates to the biological and biochemical uses of these new bistramides, in particular for cancer therapy, in particular, for solid human tumours, or the treatment of parasitic illnesses.

The bistramides according to the invention are characterized in that they are capable of exercising an anti-tumoural effect in vivo entailing the differentiation of tumoural cells, with the inhibition in vitro of the expression of the erb-2 oncogene normally expressed by the cells of the non-small cell bronchopulmonary lines.

their $LD_{50}$ is greater than 30 mg/kg, even 160 mg/kg or more, and they correspond to formula (I)

(I)

in which $R_1$, X, Y and $R_2$, identical to or different from each other, represent a saturated or unsaturated hydrocarbon chain with 1 to 20 carbon atoms, substituted by at least one —OH group and/or a ketone function, including, if appropriate, at least one ring, this ring being able to contain one or more unsaturations, $R_3$, $R_4$ and $R_5$, identical to or different from each other, are chosen from hydrogen, alkyl or alkoxy radicals with 1 to 4 carbon atoms, a —COOH, —OH, —$NH_2$ or —$NO_2$ group, or a halogen atom, it being understood that when $R_3$ and $R_4$ each represent a hydrogen atom, $R_1$ and $R_2$ do not respectively represent the following chains:

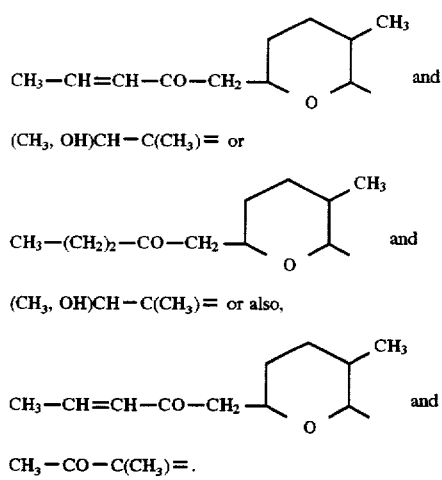

It will be remembered that the compounds corresponding to these three exclusions are bistramides A, B and C of the prior art mentioned above.

The expression "anti-tumoral activity in vivo" as used above signifies that an inhibition of the tumoural proliferation of non-small cell bronchopulmonary cancers (80% of pulmonary tumours) has been shown, without acute toxicity to the animal. These properties permit a therapeutic plateau to be obtained allowing access to the standards of the National Cancer Institute for products with $T \leq 42\%$.

C

The "$LD_{50}$" of the products of the invention has been measured for mice after injection of the products by intravenous route.

Taking into account the $LD_{50}$ value of the bistramides thus defined, bistramides A, B and C mentioned above are excluded from the scope of the invention. Moreover, it will be noted that due to their high toxicity these bistramides A, B and C would not be able to lead to, during the duration of treatment, the obtaining of the advantageous effects observed with the products of the invention.

The therapeutic index reaches a value of 5.0 for some of the bistramides of the invention.

The bistramides of the invention are also characterized in that they are capable of exerting a cytostatic activity vis-à-vis parasites.

According to a preferred provision of the invention in formula I above, $R_1$ contains 1 to 15 carbon atoms.

According to another preferred provision, $R_1$ contains one or two ethylenic double bonds.

$R_2$ preferably contains 6 to 10 carbon atoms, in particular 8 or 9, and advantageously contains an ethylenic double bond.

In yet another preferred provision, X and Y contain 2 to 8 carbon atoms, notably from 2 to 6 carbon atoms, in particular from 3 to 5.

$R_3$ and $R_5$ advantageously represent, in any one of the preceding provisions, an alkyl or alkoxy radical, in particular with 1 to 4 carbon atoms, and $R_4$ is a hydrogen atom.

A subject of the invention is also the bistramide derivatives of formula I, more particularly those allowing their use as pro-drugs. Esters and ethers will be mentioned as examples, in particular alkyl ethers with 1 to 4 carbon atoms or glycolsylated derivatives.

Particularly preferred bistramides, taking into account the importance of their therapeutic properties in vivo which will be explained in the following description, are chosen from

- bistramide D, of formula (II)

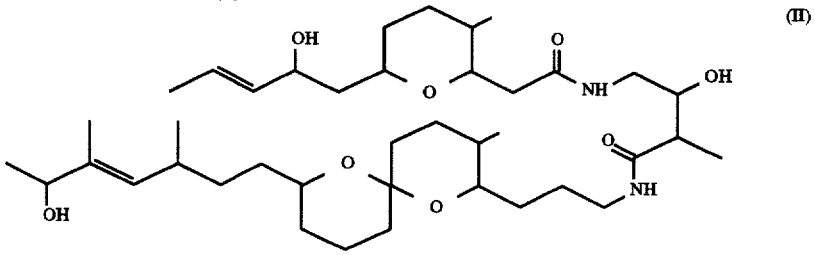

(II)

- bistramide L of formula (III)

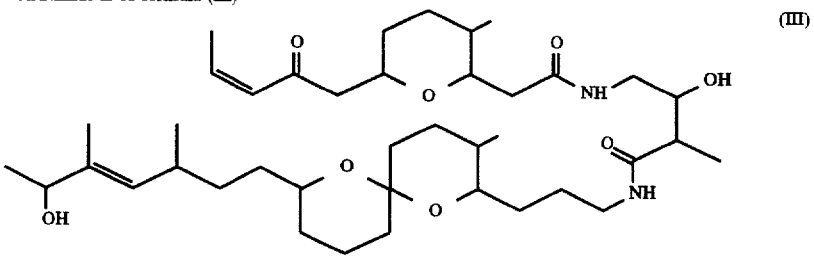

(III)

and quite particularly bistramide K of formula (IV)

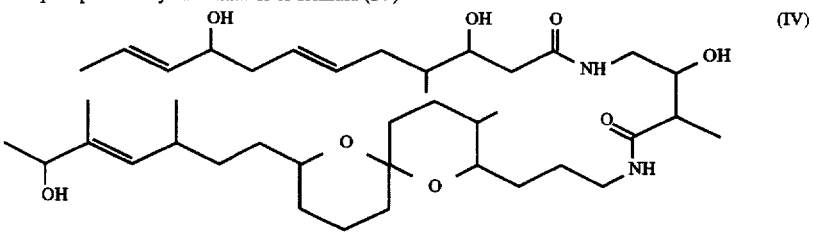

(IV)

The enantiomeric and diastereoisomeric forms, alone or in mixtures, of the bistramides defined above are also part of the invention.

It will be noted that these bistramides can exist in a dehydrated form.

Knowledge of the chemical formula of these products allows recourse to chemical synthesis processes in order to obtain them.

It is also possible to obtain bistramide D by hemisynthesis from bistramide A the unsaturated α, β ketone function of which in position 4 is particularly reactive and can be hydroxylated by reaction with a reducing agent. Modifications to the substitution chains can then be brought about by operating according to known methods.

It will be noticed that the conversion by hemisynthesis of the toxic bistramide A into the less toxic bistramide D represents an essential stage of the present invention which corresponds to the following diagram:

The nature of the chromatography column support and its granulometry, as well as the mixture or mixtures of solvents used are chosen so as to selectively separate in a few stages the biologically active bistramides. The two first fractionations are advantageously carried out on silica columns using ethyl acetate or dichloromethane type solvents, advantageously with methanol added to them.

In the final purification stage of the fractions, water is used with methanol, dichloromethane or acetonitrile type solvents.

The elution can be carried out following a gradient or as a variant in an isocratic manner.

The fractions as isolated at each stage are also a subject of the invention.

The organic extract to which this succession of stages is applied is obtained by treatment of the lyophilized powder of *L. bistratum* and/or its prochlorons with dichloromethane.

Bistramide A reducing agent

Bistramide D

Moreover, the extraction yield of bistramide A from the ascidia is of the order of 0.1%, whereas it is only 0.021% for bistramide D. The reduction reaction leads, in equivalent proportions, to two carbon 4 epimers, one of which corresponds to bistramide D. This stage is carried out with an average yield of 70%, which therefore amounts to multiplying the quantity of bistramide D available by a factor of about 1.7 (i.e. 3.5 for the 2 epimers).

A subject of the invention is also the bistramides as obtained by extraction from *L. bistratum* and/or its prochlorons, and the derivatives of these bistramides.

This extraction process includes successive fractionations by chromatography starting from an organic extract of *L. bistratum* and/or its prochlorons. These fractionations are carried out by implementing the following operations:

low pressure liquid chromatography of the dry organic extract in order to eliminate at least the majority of the impurities having a polarity greater or less than that of the sought products, high pressure liquid chromatography of the fractions rich in bistramides, in a manner so as to obtain the fractions enriched with a given bistramide, and advantageously, purification of these fractions by high pressure liquid chromatography in order to selectively isolate a given bistramide.

The prochlorons are obtained from colonies of *L. bistratum* by sieving a suspension formed by the compression of ascidiae in sea water.

The production of bistramides according to the process described above is applied to an extract as obtained after freezing, lyophilization and extraction using dichloromethane of the residue which has been separated by sieving.

Study of the pharmacological properties of the products of the invention has shown that they exert a cytostatic effect in vitro.

It is noted that on tumoural cells this effect acts according to a different mechanism to that observed with the antitumoural agents usually used in cancer chemo- therapy.

In fact, it appears that the bistramides induce an irreversible atypical terminal differentiation of the tumoural cells, resulting in the arrest of the development of the tumour.

This action which had been envisaged for A bistramide, could not however be exploited given the acute toxicity of this product. Its administration over the period of repetitive treatment, would inevitably lead to poisoning of the treated organism.

Quite to the contrary, the low toxic character of the products of the invention as regards the organism allows the differentiating effect to manifest itself in the stem cells of tumoural tissue, without unwanted effects on healthy tissue, thus allowing a therapeutic plateau to be established with a view to a treatment.

In addition, according to one aspect which is of major interest, the cytostatic effect of the bistramides of the invention is also exerted vis-à-vis parasites.

In an unexpected fashion, the bistramides cause a cessation of parasitic proliferation during the G1 phase of the cell cycle.

In particular, an anti-paludic activity was shown with these bistramides.

The interest in this activity can be measured by recalling that human paludism represents one of the foremost endemic diseases in the world, responsible for a significant morbidity and a mortality estimated currently at 1 or 3 million individuals the vast majority of which are infants living in the tropics.

The interest in producing new active molecules is as great as the spread of strains of *Plasmodium falciparum*, the lethal species, resistant vis-à-vis standard anti-malarial medicaments and that, in addition, vaccinal protection, on which significant research is carried out, will not be effective after several years.

Among the other anti-parasitic activities of these bistramides, there can be mentioned their anti-leishmanial activity.

Therefore, at a dose of 500 µg/ml, bistramide D has an anti-leishmanial activity in vitro on *L.(L) donovani*.

Therefore, a subject of the invention is the exploitation of the properties of these bistramides for the production of pharmaceutical compositions.

The pharmaceutical compositions of the invention are characterized in that they contain an effective quantity of at least one bistramide as defined above, in combination with an inert pharmaceutical vehicle. The bistramide used advantageously constitutes, due to the nature of its substituents, such as ethers or esters, a pro-drug.

If appropriate, these compositions contain the active ingredients of other medicaments. In particular, there can be mentioned their combination with medicaments containing anti-mitotic poisons of the spindle, such as vincristine, vinblastine or vinorelbine within the scope of anti-tumoural applications, or with chloroquine for the treatment of parasitic illnesses.

They will also be advantageously used in combination with compounds which facilitate their assimilation such as sugars like glucose.

The compositions of the invention are particularly suitable for the chemotherapy of cancers in which few cells are in a state of proliferation. Also they are advantageously of use for the treatment of slow development solid human tumours, which are therefore very chemoresistant, such as 80% of bronchopulmonary tumours and certain colic tumours, breast cancers and melanomas for which current therapy provides no really effective medicament.

These compositions are also of use for the treatment of parasitic illnesses, such as paludism or leishmaniasis.

Therefore, an aim of the invention is also the use of the bistramides defined above for obtaining a medicament intended for a use such as anti-parasitic.

In particular it envisages the use of these bistramides and notably those corresponding to formulae (II) to (IV), for the production of medicaments for the treatment of paludism or also leishmaniasis.

The packaging with a view to sale, in particular the labelling and instructions for use, and advantageously the container are produced as a function of the therapeutic use envisaged.

The pharmaceutical compositions of the invention can be administered in different forms, more especially by oral or injectable route.

For administration by oral route, tablets, pills, troches, capsules, drops are used in particular. These compositions advantageously contain from 10 to 100 mg of active ingredient per unit dose, preferably from 40 to 60 mg.

Other forms of administration include, solutions which are injectable by intravenous, sub-cutaneous or intramuscular route, produced from sterile or sterilizable solutions. They can also be suspensions or emulsions.

The injectable forms contain 10 to 50 mg of active ingredient per unit dose, preferably from 15 to 30 mg.

For information only, the dose which can be used in man corresponds to the following doses: thus 10 to 30 mg/day is administered to a patient, in one or two doses for the treatment of bronchopulmonary tumours.

A subject of the invention is also the biological reagents whose active ingredients are constituted by the bistramide derivatives defined above.

These reagents can be used as references or standards in studies of possible anti-tumoural or anti-parasitic activities.

Other characteristics and advantages of the invention will appear from the examples which follow related to obtaining the bistramide derivatives and from the study of their anti-tumoural and anti-parasitic activity and from reference of the single FIGURE which represents a growth curve as a function of time of pulmonary tumoural xenografts in a nude mouse after treatment with the bistramides of the invention.

EXAMPLE 1

Isolation of bistramides D, K and L by extraction from *Lissoclinum bistratum*.

A example of extraction from samples of *Lissoclinum bistratum*, accompanied by its symbiotic prochlorons, originating from the islands of Ua and N' Do, New Caledonia, is reported. These samples were cleaned of obvious debris, ground up, then lyophilized a few hours after collecting.

EXTRACTION PROCESS

Lissoclinum bistratum (5900 g) is treated 3 times with dichloromethane, at the rate of 3500 ml of solvent per kilo of lyophilized basic material, at ambient temperature and under agitation. The organic solutions are filtered, collected, then evaporated to dryness in a rotary evaporator (temperature 40° C.). The weight of the crude extract obtained is 44.2 g.

This crude extract is fractionated by low pressure liquid chromatography (silica 60–200 µm 900 g; ethyl acetate:methanol 93:7 in isocratic elution, 20 ml/min). This results in 11 fractions, of which it is fraction 9 which contains the bistramides referred to (6000° to 8000° ml, 22.3 g) (all the elution volumes mentioned in this process include the dead volume of the column).

Fraction 9 is treated by high pressure liquid chromatography (Jones Chromatography column 52×300 mm, silica 8 µm, dichloromethane:methanol 95:5 in isocratic elution at 90 ml/min, UV detection 254 nm and IR, mass injected 3 g per cycle). Among the fractions obtained, three fractions are retained: No. 1 (521° to 720° ml, 1004 mg), No. 2 (1261° to 2520° ml, 2992 mg) and No. 3 (2521° to 3780° ml, 532 mg). The intermediate fraction which is not retained (721° to 1260° ml) corresponds to A bistramide.

Batch No. 1 is purified by HPLC (Interchim column 22×250 mm, silica 10 µm; dichloromethane:methanol:water 96:3.9:0.1 at 10 ml/min, UV detection 254 nm, bistramide L rT=9 min, then Biochrom column 8×250 mm, C18 8 µm; acetonitrile:water 60:40 at 4 ml/min, bistramide L rT=16 min), which produces 171 mg of bistramide L.

Batch No. 2 is purified by HPLC (CEDI column 52×300 nm, C18 15–25 µm; methanol:water 85:15 at 85 ml/min, IR detection, bistramide D rT=22 min) and produces 1262 mg of bistramide D.

Batch No. 3 is purified by HPLC (Interchim column 22×250 mm, C18 10 µm, methanol:water 85:15 at 10 ml/min, IR detection, bistramide K rT=19 min), which produces 218 g of bistramide K.

The three products have the appearance of colourless amorphous solids. They can be subjected to thin layer chromatography (silica, dichloromethane:methanol 90:10) and revealed by a vanillin-based reagent (vanillin 1 g, pure sulphuric acid 100 ml, sprayed on the chromatograph, then this is heated for 10 minutes at 110° C., bistramide L:brown band at Rf=0.45, bistramide D:mauve band at Rf=0.41, bistramide K:mauve band at Rf=0.28).

The yields, relative to the weight of dry powder are: bistramide D: $21.4 \times 10^{-3}\%$, bistramide K: $3.7 \times 10^{-3}\%$, bistramide L: $2.9 \times 10^{-3}\%$.

EMPIRICAL FORMULAE AND MOLECULAR WEIGHTS

Bistramide D: $C_{40}H_{70}N_2O_8$, MW 706; $C_{40}H_{68}N_2O_7$ ion, MW=688.5006

Bistramide K: $C_{40}H_{70}N_2O_8$, MW 706; $C_{40}H_{68}N_2O_7$ ion, MW =688.5022

Bistramide L: $C_{40}H_{68}N_2O_8$, MW 706.4968

STRUCTURAL FORMULAE

The structural formulae given above were established on the basis of the usual spectral data (UV, IR, NMR and mass spectrometry), and by comparison with that of bistramide A as described by Foster et al. in the reference cited previously.

The results of the analysis by mass spectrometry of bistramides D and K and by NMR of bistramides D, K and L are recorded in Tables 1 and 2 which follow.

The measurements of ei (electronic impact) and of hrms (High resolution mass spectrometry) were recorded on a Varian MAT 311 at 70 keV, with a resolution of 1500.

The measurements of fab (fast atomic bombardment) are obtained on a Kratos Concept II HH apparatus. The samples are dissolved in a thioglycerol and a small drop of the sample solution is placed on the copper target of the fab direct insertion probe. The sample is bombarded with 7 keV xenon atoms. The ions produced are accelerated through a voltage of 8 kV and the negative ions are detected.

TABLE 1

| Bistramide | $M^+$ (experimental) | Formula | $M^+$ (theoretical) |
|---|---|---|---|
| D | 705 (M-1,fab) | $C_{40}H_{70}N_2O_8$ | 706 |
| K | 705 (M-1,fab) | $C_{40}H_{70}N_2O_8$ | 706 |
| D − H$_2$O | 688.5006 (ei-hrms, fab) | $C_{40}H_{68}N_2O_7$ | 688.5026 |
| K − H$_2$O | 688.5022 (ei-hrms, fab) | $C_{40}H_{68}N_2O_7$ | 688.5026 |

The ions with the highest masses observed for bistramide D and for bistramide K with ei and positive fab mass spectrometry represent the molecular ion less H$_2$O. However, the M-H ions are observed for the two metabolites in the negative fab spectrum.

The results obtained for bistramide K show that it is an isomer of bistramide D.

In Table 2, the data from the NMR analysis of bistramides D, K and L is shown. The spectra are obtained by using a $^1$H and $^{13}$C double C-5 probe in a Brüker AM 400 WB spectrometer. The pure bistramides are dissolved in CHCl$_3$ and the chemical shifts are evaluated relative to tetramethysilane (TMS).

For the experiments on $^1$H, the following parameters were retained: spectral width 2994 Hz, pulse width 3.5 µs (45°), 16 sweeps, and for those on $^{13}$C: spectral width 23809.5 Hz, pulse width 2.4 µs (45°), 1200 sweeps.

TABLE 2

| | Bistramide D | | Bistramide K | | Bistramide L | |
|---|---|---|---|---|---|---|
| | $^{13}$C (mult.) | $^1$H (J$_{HH}$ Hz) | $^{13}$C (mult.) | $^1$H (J$_{HH}$ Hz) | $^{13}$C (mult.) | $^1$H (J$_{HH}$ Hz) |
| 1 | 17.59 (q) | 1.65 (dd, 6.3; 1.4) | 17.62 (q) | 1.65 (dd, 6.4; 1.4) | 16.04 (q) | 2.05 (dd 1.6; 7.1) |
| 2 | 134.02 (d) | 5.72 (dqd, 15.7; 6.3; 1.0) | 133.53 (d) | 6.80 (15.3; 6.4; 1.0) | 144.37 (d) | 6.31 (dq, 11.4; 7.1) |
| 3 | 125.75 (d) | 5.58 (dd, 15.7; 6.3; 1.4) | 126.26 (d) | 5.46 (15.3; 6.4; 1.4) | 127.58 (d) | 6.09 (dq, 11.4; 1.5) |
| 4 | 71.95 (d) | 4.12 (t, 6.3) | 71.90 (d) | 4.04 (6.4) | 200.05 (s) | — |
| 5 | 42.86 (t) | 1.70 (m), 1.55 (m) | 40.64 (t) | 2.20 (m), 2.14 (m) | 49.38 (t) | 2.47 (dd, 3.3; 17.2), 2.72 (dd, 8.5; 17.2) |
| 6 | 69.39 (d) | 3.87 (m) | 127.68 (d) | 5.43 (14.0; 7.0) | 64.70 (d) | 4.10 (m) |
| 7 | 31.07 (t) | 1.63 (m), 1.30 (m) | 131.73 (d) | 5.47 (14.0; 7.0) | 30.31 (t) | 1.30 (m), 1.63 (m) |
| 8 | 26.43 (t) | 1.64 (m), 1.30 (m) | 36.66 (t) | 2.13 (13.5; 1.65), 1.94 (13.5; 1.65) | 26.35 (t) | 1.26 (m), 1.55 (m) |
| 9 | 32.96 (d) | 1.93 (m) | 38.40 (d) | 1.58 (m) | 33.16 (d) | 1.72 (m) |
| 10 | 16.85 (q) | 0.83 (d, 7.0) | 14.40 (q) | 0.88 (d, 6.9) | 16.92 (q) | 0.80 (d, 7, 0) |
| 11 | 74.22 (d) | 4.22 (m) | 71.43 (d) | 3.88 (dt, 8.8; 4.2) | 74.60 (d) | 4.02 (ddd, 1.8; 4.75; 11.7) |
| 12 | 33.12 (t) | 2.68 (dd, 15.0; 11.8), 2.18 | 36.66 (t) | 2.31 (m), 2.30 (m) | 32.40 (t) | 2.70 (dd, 11.45; 15.1), 2.09 |

TABLE 2-continued

|  | Bistramide D | | Bistramide K | | Bistramide L | |
|---|---|---|---|---|---|---|
|  | $^{13}C$ (mult.) | $^{1}H$ ($J_{HH}$, Hz) | $^{13}C$ (mult.) | $^{1}H$ ($J_{HH}$, Hz) | $^{13}C$ (mult.) | $^{1}H$ ($J_{HH}$, Hz) |
| 13 | 172.33 (s) | (dd, 15.0; 0.5) — | 173.64 | — | 173.42 (s) | (dd, 2.0; 15.1) — |
| 14 | 43.80 (t) | 3.48 (m) 3.29 (m) | 43.39 (t) | 3.32 (t, 5.6) | 44.51 (t) | 3.44 (ddd, 5.0; 6.5; 14.0) 3.16 (dt, 5.9; 14.0) |
| 15 | 73.11 (d, 1.9) | 3.75 (m) | 72.57 (d) | 3.68 (dt, 5.4, 5.6) | 73.64 (d) | 3.40 (m) |
| 16 | 43.19 (d) | 2.35 (m) | 43.31 (d) | 2.33 (m) | 43.29 (d) | 2.31 (dq 5.0; 7.1) |
| 17 | 15.76 (d, 8.0) | 1.21 (d, 7.0) | 15.45 (q) | 1.18 (d, 7.0) | 15.34 (q) | 1.18 (d, 7.1) |
| 18 | 175.60 (s) | — | 175.72 (s) | — | 175.10 (s) | — |
| 19 | 39.36 (t) | 3.25 (m) 3.15 (m) | 39.40 (t) | 3.24 (m) 3.19 (m) | 39.39 (t) | 3.21 (q, 6.8) |
| 20 | 25.59 (t) | 1.70 (m) 1.50 (m) | 25.56 (t) | 1.78 (m) 1.50 (m) | 25.68 (t) | 1.47 (m), 1.74 (m) |
| 21 | 30.24 (t) | 1.64 (m) 1.27 (m) | 30.22 (t) | 1.65 (m) 1.31 (m) | 30.50 (t) | 1.33 (m), 1.63 (m) |
| 22 | 74.17 (d) | 3.13 (dt, 6.9; 2.0) | 74.16 | 3.12 (dt, 9.6; 2.1) | 74.17 (d) | 3.08 (dt, 2.3; 9.6) |
| 23 | 34.84 (d) | 1.20 (m) | 34.76 (d) | 1.26 (m) | 34.72 (d) | 1.24 (m) |
| 24 | 17.95 (q) | 0.78 (d, 6.5) | 17.91 (q) | 0.78 (d, 6.5) | 17.87 (q) | 0.74 (d, 6.5) |
| 25 | 27.85 (t) | 1.58 (m) 1.45 (m) | 27.75 (t) | 1.56 (m) 1.42 (m) | 27.79 (t) | 1.37 (m) |
| 26 | 36.09 (t) | 1.61 (m) 1.47 (m) | 35.98 (t) | 1.60 (m) 1.43 (m) | 35.98 (t) | 1.44 (m), 1.56 (m) |
| 27 | 95.50 (s) | — | 95.48 (s) | — | 95.36 (s) | — |
| 28 | 35.41 (t) | 1.53 (m) 1.31 (m) | 35.30 (t) | 1.53 (m) 1.35 (m) | 35.35 (t) | 1.31 (m), 1.52 (m) |
| 29 | 19.22 (t) | 1.75 (m) 1.50 (m) | 19.14 (t) | 1.76 (m) 1.52 (m) | 19.09 (t) | 1.48 (m), 1.74 (m) |
| 30 | 31.24 (d) | 1.55 (m) 1.12 (m) | 31.17 (t) | 1.49 (m) 1.22 (m) | 31.22 (t) | 1.05 (m), 1.47 (m) |
| 31 | 69.13 (d) | 3.35 (m) | 68.98 (d) | 3.40 (bt) | 68.96 (d) | 3.37 (m) |
| 32 | 34.01 (t) | 1.29 (m) 1.42 (m) | 33.87 (t) | 1.40 (m) 1.25 (m) | 33.96 (t) | 1.23 (m), 1.36 (m) |
| 33 | 33.48 (t) | 1.40 (m) 1.30 (m) | 33.35 (t) | 1.35 (m) 1.30 (m) | 33.37 (t) | 1.28 (m) |
| 34 | 31.82 (d) | 2.32 (m) | 31.65 | 2.31 (m) | 31.73 (d) | 2.31 (m) |
| 35 | 20.89 (q) | 0.95 (d, 6.8) | 20.83 (q) | 0.91 (d, 4.7) | 20.85 (q) | 0.88 (d, 6.6) |
| 36 | 131.14 (d) | 5.20 (d, 9.3) | 131.13 (d) | 5.15 (d, 9.40) | 131.17 (d) | 5.11 (d quint, 9.4, 1.1) |
| 37 | 137.15 (s) | — | 137.04 (s) | — | 137.11 (s) |  |
| 38 | 11.95 (q) | 1.57 (fd, 1.3) | 11.81 (q) | 1.58 (fd, 1.3) | 11.66 (q) | 1.55 (d, 1.4) |
| 39 | 73.22 (d) | 4.16 (m) | 73.03 (d) | 4.15 (q, 6.4) | 73.09 (d) | 4.05 (m) |
| 40 | 21.78 (q) | 1.25 (d, 6.3) | 21.74 (q) | 1.21 (d, 6.3) | 21.69 (q) | 1.18 (d, 6.5) |
| NH 13/14 |  | 7.05 (bt, 5.9) |  | 7.12 (bt, 6.5) |  | 7.44 (bt, 6.1) |
| NH 18/19 |  | 6.75 (bt, 5.5) |  | 6.80 (bt, 5.6) |  | 6.89 (bt, 5.8) |
| OH 4 |  | n.o |  | n.o | n.o. |  |
| OH 11 |  | — |  | n.o |  | — |
| OH 15 |  | 4.62 |  | 4.88 |  | 4.60 (large) |
| OH 39 |  | n.o. |  | 2.85 |  | 3.65 (large) |

EXAMPLE 2

Obtaining the prochlorons from colonies of *L. bistratum*

The ascidiae are detached from their support, carefully cleaned with plenty of water to clean them of silt and other debris. They are drained, opened individually with a knife, squeezed by hand, then mechanically in a sea water bath. The suspension in sea water is filtered through a finer and finer sieve (123, 63, 40 10 and 5 µm). The prochlorons are retained by the 10 µm sieve. The residue of algae is frozen, lyophilized and extracted with dichloromethane. The obtaining of the bistramides from this extract is carried out according to the same process as from the extract of complete ascidiae.

EXAMPLE 3

Preparation of bistramide D by the reduction of bistramide A.

A solution of 50 mg (0.07 mole) of bistramide A in 3 ml of THF is cooled down in an ice bath. The bistramide A is obtained by operating according to Gouiffes et al. in Toxicon, 1988, volume 26, pages 1129–1136.

13 mg (0.35 mole) of sodium borohydride is added. After agitation for 2 hours at ambient temperature, the crude reaction medium is poured into 5 ml of water +ice, then extracted twice with 5 ml of ethyl acetate. After drying over MgSO$_4$, the solvent is evaporated off and the residue is purified by chromatography on a silica column eluted with a dichloromethane:methanol (95:5) mixture.

The first fractions contain the epimer of bistramide D (16 mg; 32%). Bistramide D (18 mg; 36%) is then recovered. The total yield of reduced products is 68%.

As a variant, the operation is carried out as indicated above, but by replacing the sodium borohydride with potassium borohydride. The total yield of reduced products is 72%.

According to another variant, 53 mg (0.07 mmoles) of bistramide A is dissolved in 3 ml of methanol containing 10% acetic acid. After the solution has been cooled down in an ice bath, 13 mg (0.21 mmoles) of potassium cyanoborohydride is added. After agitation for 4 hours under an inert atmosphere, the reaction medium is poured into 5 ml of water+ ice, then extracted twice with 5 ml of ethyl acetate. After drying over MgSO$_4$, the solvent is evaporated off and the residue is purified by chromatography on a silica column eluted with a dichloromethane:methanol (95:5) mixture.

The epimer of bistramide D is eluted first (18 mg; 34%), then bistramide D is collected (21 mg; 39%). The total yield of reduced products is 78%.

EXAMPLE 4

Study of the pharmacodynamic effects of bistramides D, K and L in vitro and in vivo Effects in vitro The cytoxicity results are recorded hereafter as the IC$_{50}$ in µg/ml (concentration corresponding to a 50% inhibition of cell growth) on 6 tumoural lines namely KB, P388, P388/dox (resistant to doxorubicin), B16 and H429 and NSCLC-N6, which are human cells of non-small cell bronchopulmonary carcinoma type.

The determinations were carried out according to the protocol given in Cancer Chemother. Pharmacol. (1991) 28:283–292 by Roussakis et al.

|  | Bistramide D | Bistramide K | Bistramide L |
|---|---|---|---|
| KB | 10.00 | >10 | 0.72 |
| p388s | 0.36 | 0.57 | 0.48 |
| p388r | 5.82 | >10 | 0.12 |
| B16 | 0.10 | 1.90 | 2.4 |
| HT 29 | 2.76 | 5.60 | 0.29 |
| NSCLC.N6-L16 | 3.43 | 3.23 | 0.12 |

The cytostatic effect of the products at the level of the cell cycle was also studied using cytofluorimetry.

The technique used corresponds to that reported by Roussakis et al. in the reference mentioned above.

An anti-proliferative effect of the products is noted linked to an irreversible blockage in the G1 phase, leading to the death of non-small cell bronchopulmonary tumoural cells (NSCLC-N6).

The G1 phase blocking is followed by passing to the G1DT phase, which characterizes the state of terminal differentiation. The cells which reach this G1DT phase produce an anti-proliferative, intracytoplasmic substance of a proteinaceous nature, which is the product of the expression of a specific gene, which probably plays the role of an anti-oncogene.

When the NSCLC-N6 cells are induced into terminal differentiation under the effect of the bistramides of the invention, one observes, in fact, the in vitro inhibition of the expression of the erb-b2 oncogene, usually expressed by the experimental model used, and of its expression product, the c-erb-b2 oncoprotein.

Effects in vivo

The anti-tumoural activity of the products of the invention was studied against solid tumours of NSCLC type grafted onto a nude mouse (D. Riou, C. Roussakis, J. F. Biard, J. F. Verbist: "Comparative study of antitumor activity of bistramides A, D and K against non-small cell bronchopulmonary carcinoma", Anticancer Research, 1993, 13, 2321–2334). Each mouse received 0.2 ml of a cell solution obtained by the mechanical dispersion of about 1 g of excised mouse tumour in 4.8 ml of a sterile saline solution. The subcutaneous grafted tumours were measured over their long length L and their short length l. The tumoural volume was evaluated according to the formula Vt=L×l$^2$/2. The tumoural growth on day d was calculated by the formula Vt$_d$/Vt$_{d0}$ for each mouse, Vt$_{d0}$ being the tumoural volume at the start of treatment.

BRIEF DESCRIPTION OF DRAWINGS

The single FIGURE shows the tumoural growth curves as a function of time (days) obtained with or without treatment with the bistramides.

The curve "____●____" relates to the control experiment, the curves "--- ♦---", "-- □--" and "-- ■--" to experiments with 10, 20 and 5 mg/kg of bistramide D respectively and the curve "----*----" to an experiment with 10 mg/kg of bistramide K. Each point represents the average tumoural growth for 6 mice.

In these experiments, bistramide K is injected at the rate of 10 mg/kg by intraperitoneal route for 16 days and bistramide D at the rate of 5 mg/kg by intraperitoneal route every day for 16 days; at 10 mg/kg by intravenous route on days 1, 5, 9, 14, and at 20 mg/kg by intravenous route on days 1, 5, 9, 14.

Examination of these curves shows that relative to the controls (100%), the tumoural growth settles, at the end of 30 days, for the treated animals at:

| | | |
|---|---|---|
| bistramide D | (5 mg/kg, IP): | 100% |
| | (10 mg/kg, IV): | 76% |
| | (20 mg/kg, IV): | 53% |
| bistramide K | (10 mg/kg, IP): | 49% |

It will be noted that bistramide A used under the conditions recorded above, is too toxic for an anti-tumoural effect to be observed.

EXAMPLE 5

Preparation of an injectable solution of bistramide D.

2 g of bistramide D is dissolved in 1000 ml of apyrogenic physiological solute. The solution obtained is distributed, under aseptic conditions, into 10 ml ampules containing 20 mg of product per ampule.

EXAMPLE 6

Anti-parasitic activity of the bistramides of the invention.

The results of experiments carried out on an in vivo model using *Plasmodium vinckei petteri*, a rodent plasmodial species kept on female white mice are recorded, these results are of interest due to a perfect synchronization of the endoerythrocytic cycle.

1. the rodents

The animals used are SWISS (IFFA CREDO) female white mice weighing approximately 30 grams. Five mice are distributed per batch.

2. the strain

The species *Plasmodium vinckei petteri* used comes from the strain 279 BY (see article by Cambie G et al. in CR.Acad.Sci.PARIS 310, series III, 183–188). This plasmodia carries out a schizogonic cycle in 24 hours in a synchronous fashion. Using the freezing-thawing technique for infected blood, only the merozoite stage resists, the other forms being destroyed.

If the injection of merozoites takes place at 0 h, the following predominant stages are observed successively:

at 3 h the ring stage (R)

at 6 h the young trophozoite stage (YT)

at 12 h the middle trophozoite stage (MT)

at 18 h the old trophozoite stage (OT)

The maturation of the parasite in the red blood corpuscle, from the ring stage to the old trophozoite stage corresponds to the G1 phase of the cell cycle.

This phase is followed by the multiplication of the parasite, S and M phases of the cell cycle.

The schizont stage corresponds to the bursting and release of the merozoites.

Observation of blood parasites takes place on stained smears carried out by taking a drop of blood from the tail. The smears are then stained with May-Grumwald-Giesma. Calculation of the parasitemia (number of parasites per 100 red blood corpuscles) is carried out on smears.

The studies undertaken required the formation of a stock of parasitized blood, stored at −70° C. in liquid nitrogen. Blood is removed from the infested mice via the retro-orbital sinus using a heparinized pasteur pipette. A 10% glycerol solution is added volume for volume with the parasitized blood. The blood is then distributed into freezing tubes at the rate of 0.5 ml per tube.

3. injection of bistramide

In these trials bistramide D is used in sterile physiological water containing 5% DMSO.

The product is injected by sub-cutaneous route in the thigh.

4. Proof of activity

A/ PETERS test

In order to verify the activity of the compound studied, the PETERS test is used which constitutes the reference for the screening of molecules with anti-malarial activity. (PETERS W. 1980. Chemotherapy and Drug resistance in Malaria, vol II. Academic Press).

After treatment for 4 days, the percentage of red blood corpuscles parasitized is compared on thin smears between the control batch and the treated batch. In this way a percentage inhibition is established.

Methodology a) injection of $10^7$ of parasitized red blood corpuscles by I.P. route (D0)

b) injection of Bistramide D at 15 mg/kg/day, for 4 days by sub-cutaneous route (D0, D1, D2, D3)

c) checking the parasitemia on smears on D4

| Results | | |
|---|---|---|
| | trial A: | |
| i.e. 85% inhibition | controls on D4 | 4% parasitemia |
| | treated batch on D4 | 0.64% parasitemia |
| | trial B: | |
| i.e. 87% inhibition | controls on D4 | 4% parasitemia |
| | treated batch on D4 | 0.50% parasitemia |
| | trial C | |
| i.e. 81% inhibition | controls on D4 | 1.2% parasitemia |
| | treated batch on D4 | 0.23% parasitemia |

Examination of the results obtained in the three trials above, shows an average inhibition of 84% when a bistramide according to the invention is administered.

B/ STUDY OF THE PARASITIC STAGE SUSCEPTIBLE TO BISTRAMIDES

In order to appreciate the parasitic stage or stages the most susceptible to the action of the bistramides of the invention, the effect of these bistramides was studied on each parasitic stage predominant during the cell cycle for a given species of Plasmodium.

The results given hereafter concern the effect of bistramide B on the parasitic stages of *Plasmodium vinckei petteri*.

Methodology

After infestation of the mice, five batches of five mice are constituted. Each batch is treated with a dose of 15 mg/kg of bistramide D at the moment when one of the stages predominates.

In addition, the following batches are prepared: one control batch, one batch of merozoites, one ring batch, one batch of young trophozoites, one batch of middle trophozoites and one batch of old trophozoites.

The following are evaluated: the retardation of parasitemia or the patent period as the time in days necessary for the parasitemia to reach 1%.

Results:

| | |
|---|---|
| control batch | 5 D |
| merozoite batch | 5 D |
| ring batch | 5.4 D |
| young trophozoite batch | 5.6 D |
| middle trophozoite batch | 6.25 D |
| old trophozoite batch | 6.2 D |

The KRUSKAL-WALLIS unilateral statistical test (BDMP, Statistical software manual 1990, vol. 1 Ed WJ DIXON U. of California Press) shows a significant difference ($p<0.001$) between the control batch and the middle and old trophozoite batches.

Therefore a selective activity of bistramide D is observed on the middle and old trophozoite stages.

According to a preliminary flow cytometry study of the murine red blood corpuscles parasitized by the species *Plasmodium vinckei petteri* which shows, in the presence of bistramide D, a partial blocking of the parasite at its maturation stage. The consequence of this is to halt the proliferation at the middle and old trophozoite stage.

This blocking, which corresponds to the G1 phase of the cell cycle, is dose dependent, and is probably linked to an atypical maturation of the parasite.

C/ COMPARISON OF MONODOSE AND MULTIDOSE THERAPEUTIC SCHEMA

The object is to monitor the parasitemia on a daily basis and to evaluate the inhibition of the parasitemia according to the therapeutic schema adopted for the treatment. The following are shown: the morphological modifications of the parasite by the parasitic formula, calculation of the parasitic formula is also carried out on smears and allows the evaluation of each stage:ring, young trophozoite, middle trophozoite, old trophozite for 100 red blood corpuscles.

The methodology used is as follows:

a) after infestation, three batches of five mice are constituted, namely a control batch, at D0 a so-called monodose batch, for which a single injection of bistramide D (15 mg/kg) is given to the mouse on D0 a so-called multidose batch, where the injection of bistramide D is carried out by administering five doses on D0, D1, D2, D3, D4 respectively (total dose 15 mg/kg)

b) the preparation and reading of the smears is carried out every day for 21 days.

The percentage of parasitemia and the percentage inhibition of the development of the parasite is determined for each batch.

The results obtained are given in Tables 1 and 2.

TABLE 1

| Day | Controls | Monodose | Multidoses |
|---|---|---|---|
| D0 | — | — | — |
| D1 | — | — | — |
| D3 | 0.33 | 0.16 | 0.12 |
| D4 | 1.2 | 0.80 | 0.2 |
| D5 | 5.5 | 3.5 | 1.6 |
| D7 | 50 | 64 | 7.4 |
| D8 | 67 | 56 | 74 |
| D9 | 48 | 42 | 67 |
| D10 | 1 | 1 | 30 |

TABLE 2

| Day | Monodose | Multidoses |
|---|---|---|
| D3 | 51.5 | 63.6 |
| D4 | 33.3 | 83.3 |
| D5 | 36.3 | 70.9 |
| D7 | 0 | 85.2 |
| D8 | 16.4 | 0 |
| D9 | 12.5 | 0 |
| D10 | 0 | 0 |

The parasitic formulae in each batch are given on D5 and on D7 in Table 3.

TABLE 3

| | Control | | Monodose | | Multidose | |
|---|---|---|---|---|---|---|
| Stage | D5 | D7 | D5 | D7 | D5 | D7 |
| R | 72.5% | 58% | 40% | 47% | 25% | 7% |
| YT | 17.5% | 17% | 37% | 31% | 28% | 0% |
| MT | 7% | 15% | 14% | 14% | 40% | 0% |
| OT | 3% | 10% | 9% | 6% | 7% | 93% |

All of these results show a very noticeable difference on D7 where the parasitemia of the multidose batch is ten times less relative to the control batch (the percentage inhibition is 85%).

The parasite is essentially found in the old trophozoite form (93%) in the multidose batch and in ring form in the control batch.

Therefore, it appears that the parasite is blocked in the old trophozoite stage.

From D8, the parasitemia between the two batches is comparable, the Plasmodium apparently being no longer effected by D bistramide.

The last injection of the drug in this multidose batch is carried out on D4, the duration of the action of bistramide D is about 3 days. This appears to be confirmed with the monodose batch: on D4 (three days after injection of bistramide D) no difference is observed between the parasitemia of the control batch and that of the monodose batch.

We claim:

1. A compound of the formula (I)

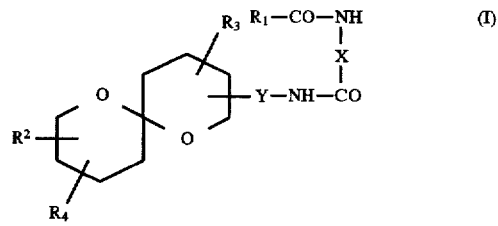

in which $R_1$ and $R_2$, identical to or different from each other, represent a saturated or unsaturated hydrocarbon chain with 1 to 20 carbon atoms, substituted by at least one group selected from an —OH group, a ketone group, and optionally, at least one

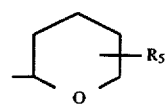

ring, this ring being able to contain one or more unsaturations,

X and Y, identical to or different from each other represent a saturated or unsaturated hydrocarbon chain with 1 to 20 carbon atoms, optionally substituted by at least one group selected from an —OH, a ketone group and at least one

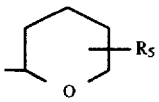

ring, this ring being able to contain one or more substitutions, $R_3$, $R_4$ and $R_5$, identical to or different from each other, are chosen from hydrogen, alkyl or alkoxy radicals with 1 to 4 carbon atoms, a —COOH, —OH, the corresponding ethers or esters, —NH$_2$, —NO$_2$ group, or a halogen atom, with the proviso that when $R_3$ and $R_4$ each represent a hydrogen atom, $R_1$ and $R_2$ do not respectively represent the following chains:

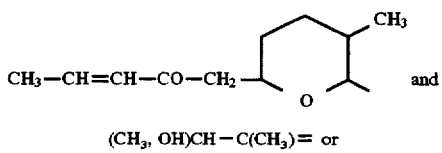

(CH$_3$, OH)CH—C(CH$_3$)= or

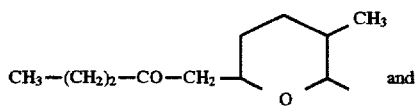

-continued
(CH$_3$, OH)CH—C(CH$_3$)= or,

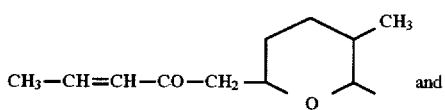

CH$_3$—CO—C(CH$_3$)=.

and with the further proviso that when $R_3$ is CH$_3$ and $R_4$ is H $R_1$ and $R_2$ do not respectively represent

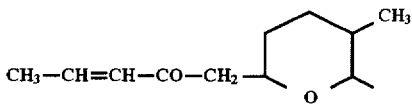

and

CH$_3$CH(OH)C(CH$_3$)=CHC(CH$_3$)CH$_2$CH$_2$.

2. A compound according to claim 1, wherein $R_1$ contains 1 to 15 carbon atoms.

3. A compound according to claim 2, wherein $R_1$ contains an ethylenic double bond.

4. A compound according to claim 1, wherein $R_2$ contains 6 to 10 carbon atoms.

5. A compound according to claim 1, wherein X and Y contain 2 to 8 carbon atoms.

6. A compound according to claim 1, wherein $R_3$ and $R_5$ represent an alkyl or alkoxy radical and $R_4$ is a hydrogen atom.

7. Bistramide K of formula (IV)

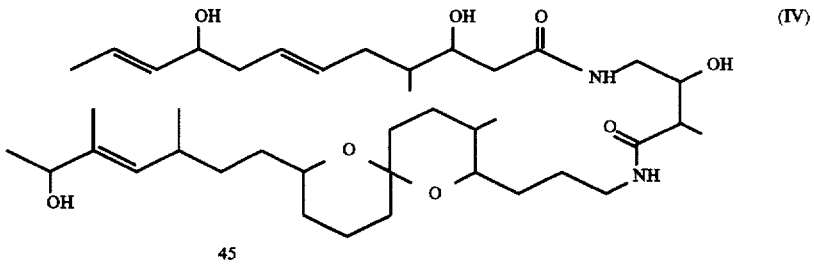

8. Bistramide D, of formula (II)

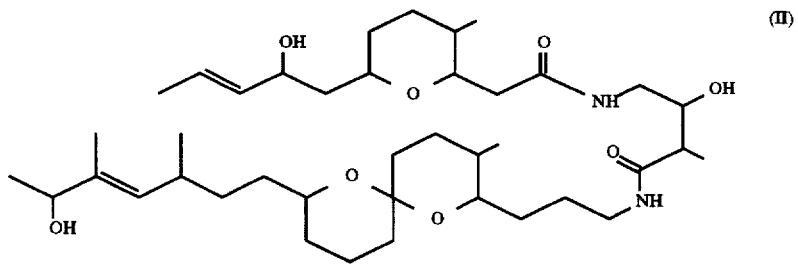

9. A compound according to claim 1, wherein said compound is in enantiomeric or diastereomeric forms.

10. A pharmaceutical composition comprising an effective quantity of a compound according to claim 1, in combination with a pharmaceutical vehicle.

11. A pharmaceutical composition according to claim 10, wherein the composition can be administered by oral or injectable route.

12. A pharmaceutical composition according to claim 11, wherein the composition is in the form of troches, tablets, capsules or pills, and that they contain from 10 to 100 mg of said compound per unit dose.

13. A pharmaceutical composition according to claim 11, wherein the composition is an injectable solution, comprising per unit dose from 10 to 50 mg of said compound.

14. A method of treating paludism or leishmaniasis by administering an effective amount of a compound according to claim 1.

15. Process for obtaining bistramides according to claim 1 by extraction from *L. bistratum*, or its symbiotic prochlorons comprising the following stages:

low pressure liquid chromatography of the dry organic extract in order to eliminate at least the majority of the impurities having a polarity greater or less than that of the sought products, high pressure liquid chromatography of the fractions rich in bistramides, in a manner so as to obtain the fractions enriched with a given bistramide, and purification of these fractions by high pressure liquid chromatography in order to selectively isolate a given bistramide the two first fractionations being are carried out on silica columns using ethyl acetate or dichloromethane type solvents, and in the final purification stage of the fractions, by using water with methanol, dichloromethane or acetonitrile type solvents.

16. Process for obtaining bistramide D according to claim 8, comprising the reaction of bistramide A with a reducing agent in order to convert the unsaturated α, β ketone function in position 4 into an —OH group.

17. A compound according to claim 1, the $LD_{50}$ of which is greater than 160 mg/kg.

18. A compound according to claim 2, wherein $R_1$ contains two ethylenic double bonds.

19. A compound according to claim 4, wherein $R_2$ contains 8 or 9 carbon atoms.

20. A compound according to claim 19, wherein $R_2$ further contains an ethylenic double bond.

21. A compound according to claim 5, wherein X and Y, contain 3 to 5 carbon atoms.

22. A compound according to claim 6, wherein said alkyl or alkoxy radical has 1 to 4 carbon atoms.

23. A pharmaceutical composition comprising an effective amount of Bistramide D according to claim 7 and a pharmaceutically acceptable carrier.

24. A pharmaceutical composition according to claim 12 containing 40 to 60 mg of said compound per unit dose.

25. A pharmaceutical composition according to claim 13, containing 15 to 30 mg of said compound per unit dose.

26. A method of treating tumors comprising administering a composition of claim 10 to a patient in need of said treatment.

27. The method according to claim 26 wherein said tumors are solid tumours.

28. A method of treating parasite infections comprising applying the pharmaceutical composition according to claim 10 to a patient in need of said treatment.

29. The method according to claim 28, wherein said parasitic infection includes paludic activity.

30. The method according to claim 28, wherein said parastic activity includes leishmanial activity.

31. The process of claim 15 wherein the two first fractionations are carried out on silica columns using solvents selected from ethylacetate or dichlorometane.

32. The process of claim 31 wherein methanol is added to said solvents.

33. The process of claim 15 wherein the final purification stage of the fraction is carried out with water containing a solvent selected from methanol, dichloromethane or acetonitrile.

* * * * *